(12) United States Patent
Bromwich

(10) Patent No.: US 7,490,611 B2
(45) Date of Patent: Feb. 17, 2009

(54) DEVICE FOR THE TREATMENT OF VERTIGO

(76) Inventor: Matthew Alexander Bromwich, 52 Elmwood Ave. E., London, Ontario (CA) N6C 1J3

(*) Notice: Subject to any disclaimer, the term of this patent is extended or adjusted under 35 U.S.C. 154(b) by 59 days.

(21) Appl. No.: 11/786,690

(22) Filed: Apr. 12, 2007

(65) Prior Publication Data
US 2007/0261702 A1    Nov. 15, 2007

(30) Foreign Application Priority Data
May 12, 2006  (CA) ................... 2546829

(51) Int. Cl.
A61B 19/00    (2006.01)

(52) U.S. Cl. .................................... 128/897

(58) Field of Classification Search ......... 128/897–898; 600/300–301, 558, 559, 595
See application file for complete search history.

(56) References Cited

U.S. PATENT DOCUMENTS

| | | | |
|---|---|---|---|
| 4,984,579 A | 1/1991 | Burgert et al. | 128/747 |
| 5,966,680 A | 10/1999 | Butnaru | 702/150 |
| 6,029,670 A | 2/2000 | Anthony | 128/897 |
| 6,568,396 B1 | 5/2003 | Anthony | 128/897 |
| 6,758,218 B2 | 7/2004 | Anthony | 128/897 |
| 2003/0116166 A1 | 6/2003 | Anthony | 128/897 |
| 2004/0097839 A1* | 5/2004 | Epley | 600/595 |
| 2007/0161875 A1* | 7/2007 | Epley | 600/301 |

FOREIGN PATENT DOCUMENTS

CA    2 386 835    5/2001

OTHER PUBLICATIONS

"The Canalith Repositioning Procedure" Headband Device, John Li, M. D. and John Epley, M.D., printout from http://users.aol.com/inventmd/bppv.html, Dec. 2000.

The Epley Omniax™ device, printout from www.vesticon.com, Dec. 2007.

The VertiGONE Goggle, printout from www.vertigone.com, Mar. 2006.

* cited by examiner

Primary Examiner—John P Lacyk
(74) Attorney, Agent, or Firm—Waddey & Patterson, P.C.; Emily A. Shouse

(57) ABSTRACT

A device for the treatment of vertigo or dizziness comprises a fluid-filled tube containing a communicating means such as a bead that passes through the tube. The tube is attached to the user's head so as to allow the user to see the entire tube and communicating means, and the tube is shaped so that the communicating means will only travel through the tube from end to end if the user performs a particle repositioning maneuver.

16 Claims, 11 Drawing Sheets

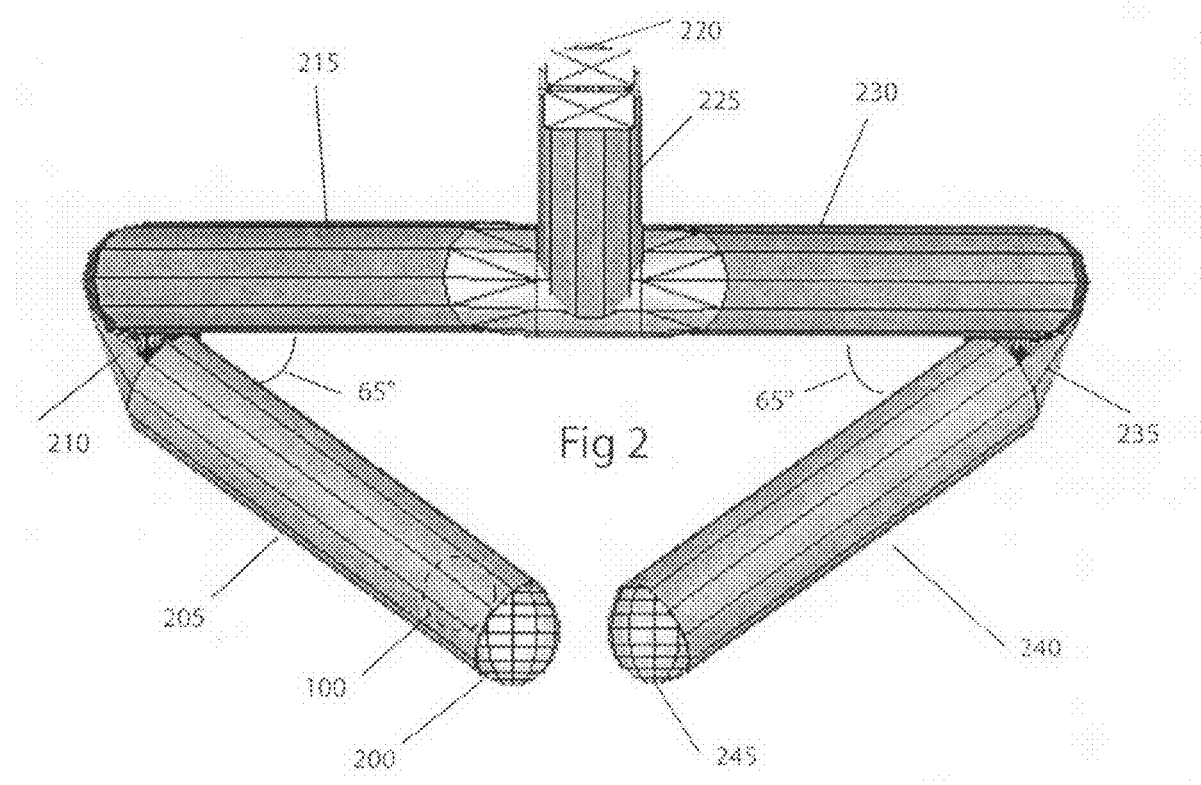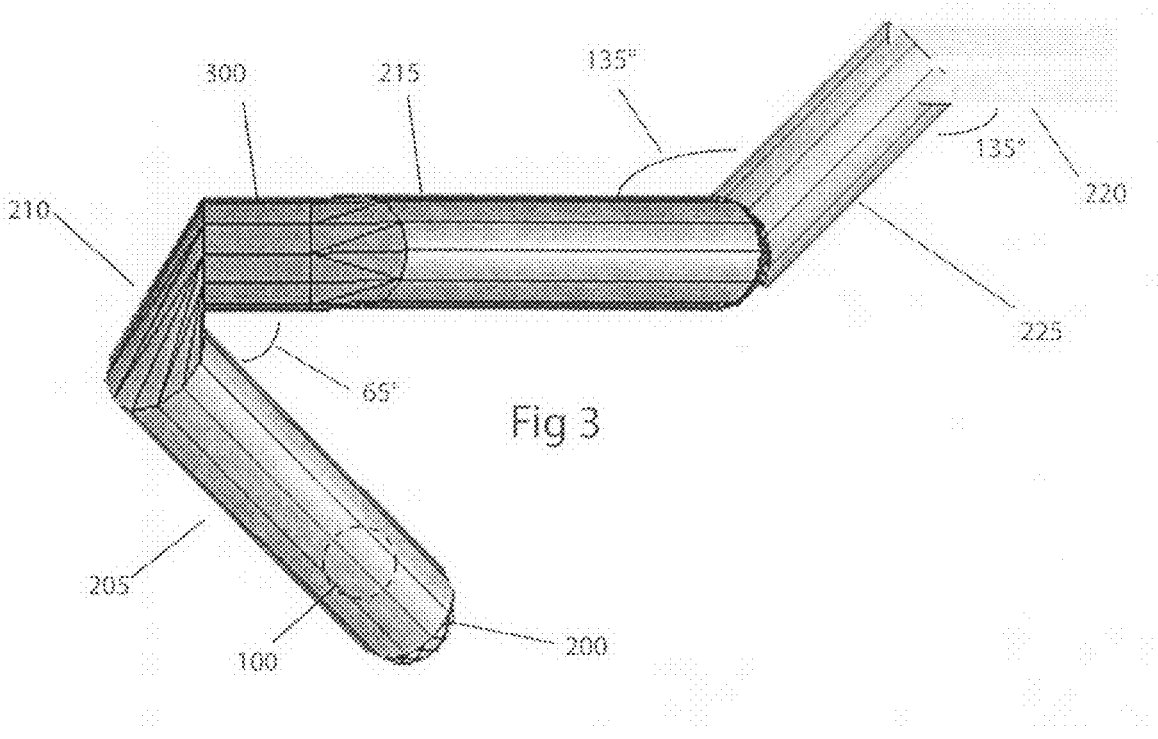

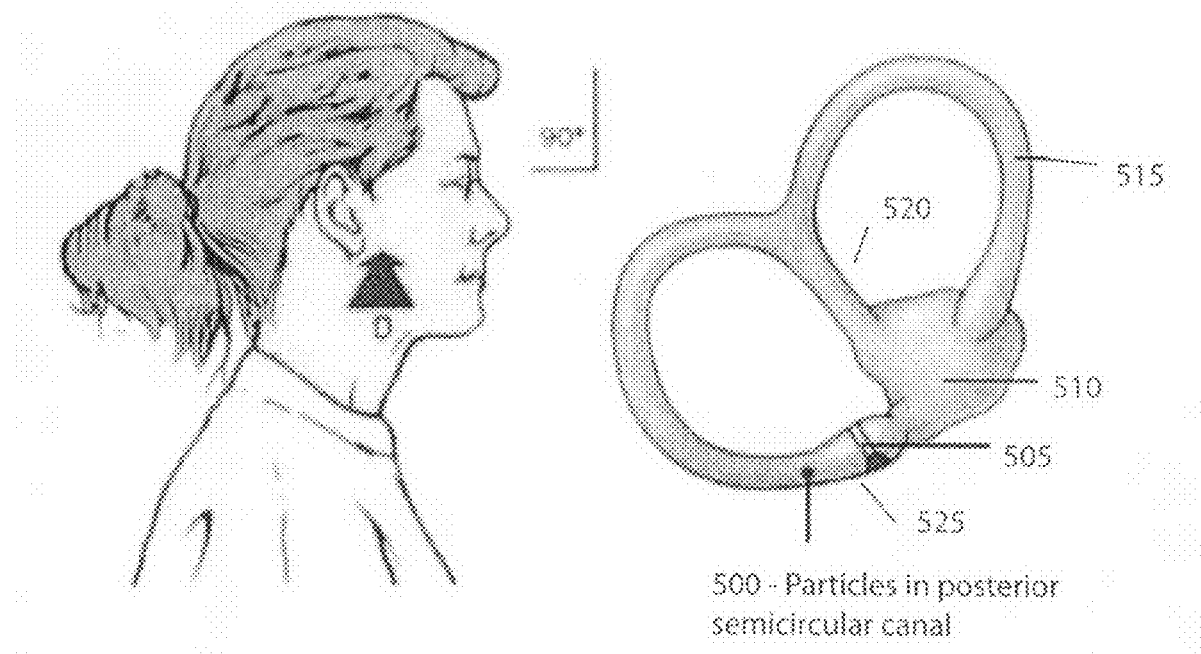
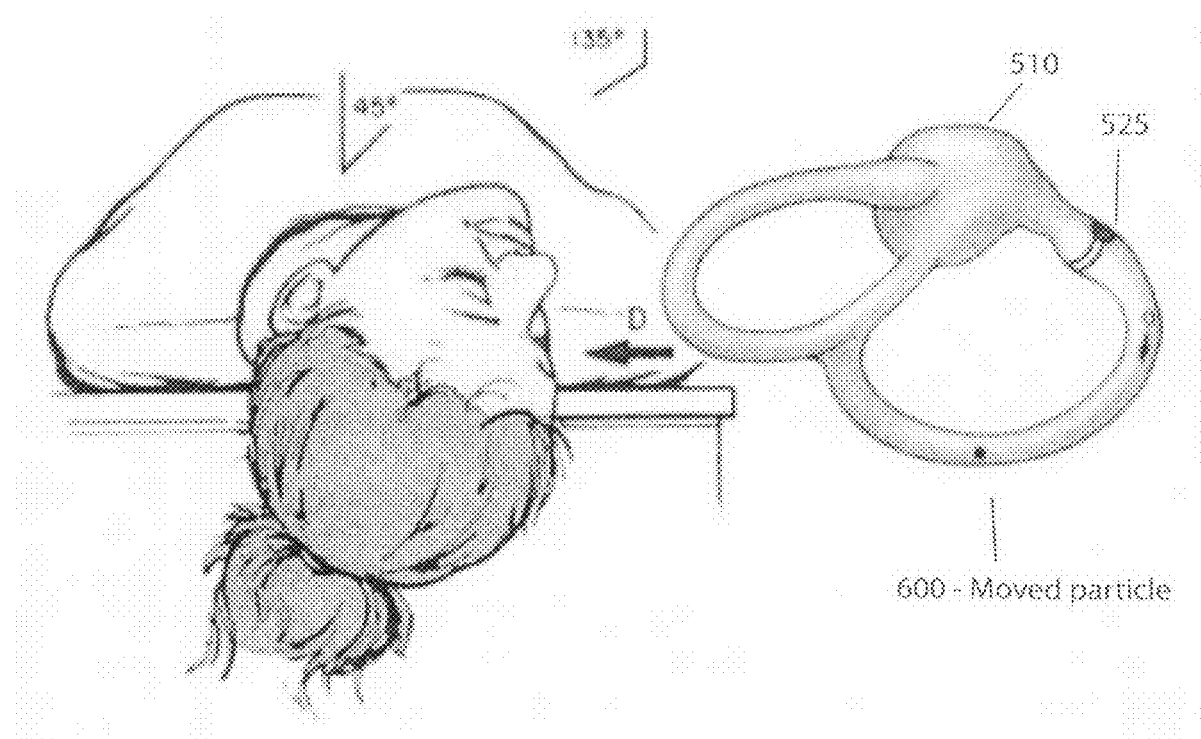

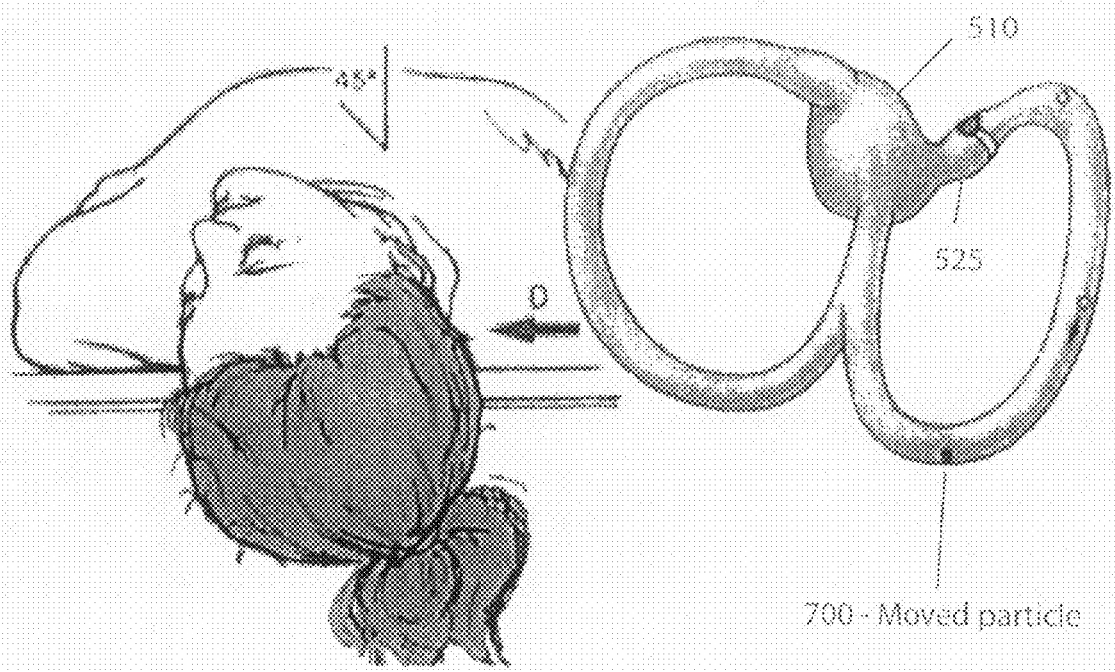
Fig 8 Supine Position 3
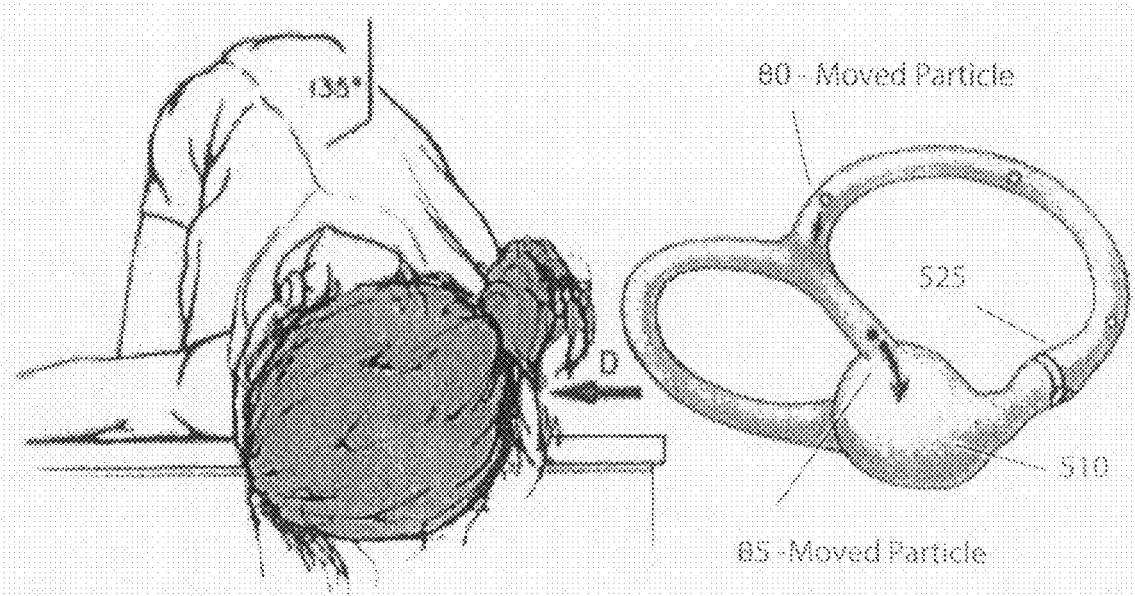
Fig 9 Supine Position 4

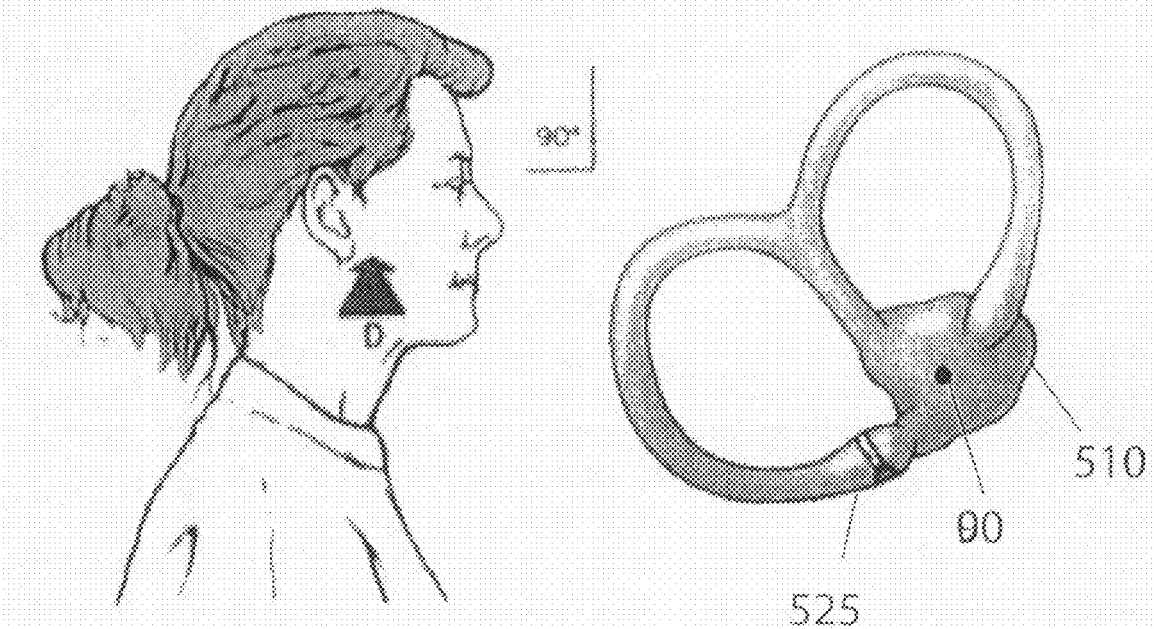
Fig 10 - Upright Position 5
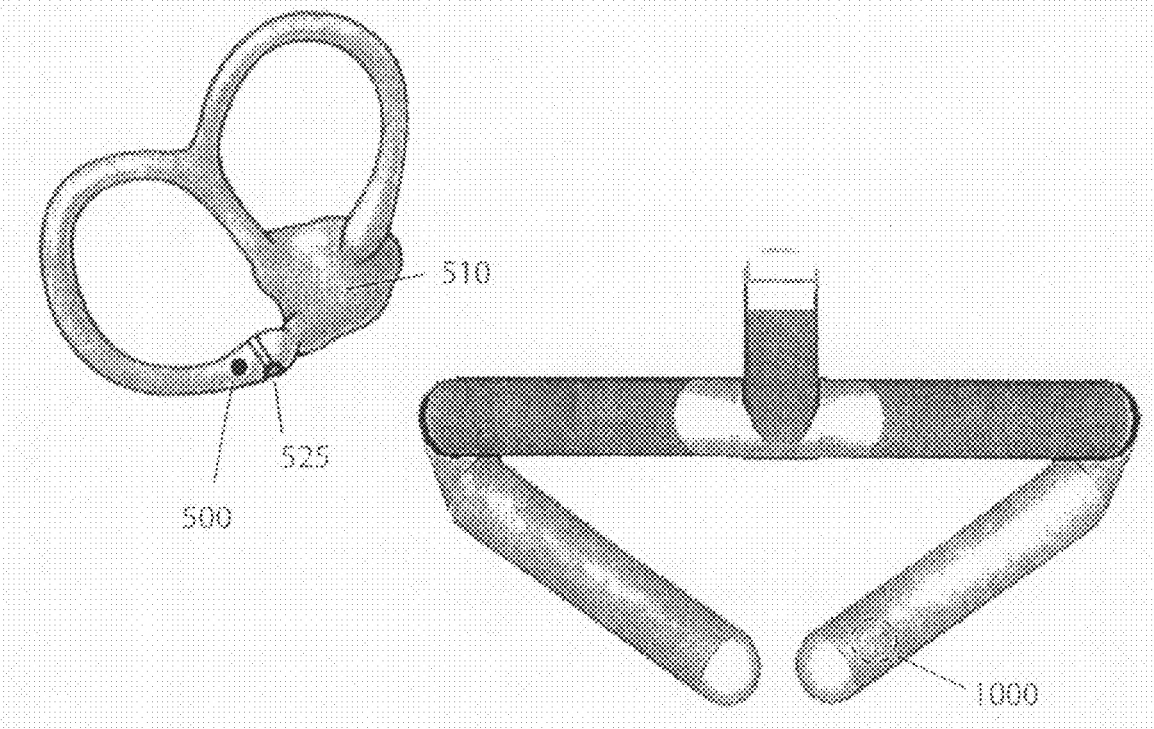
Fig 11 - Device Position 1

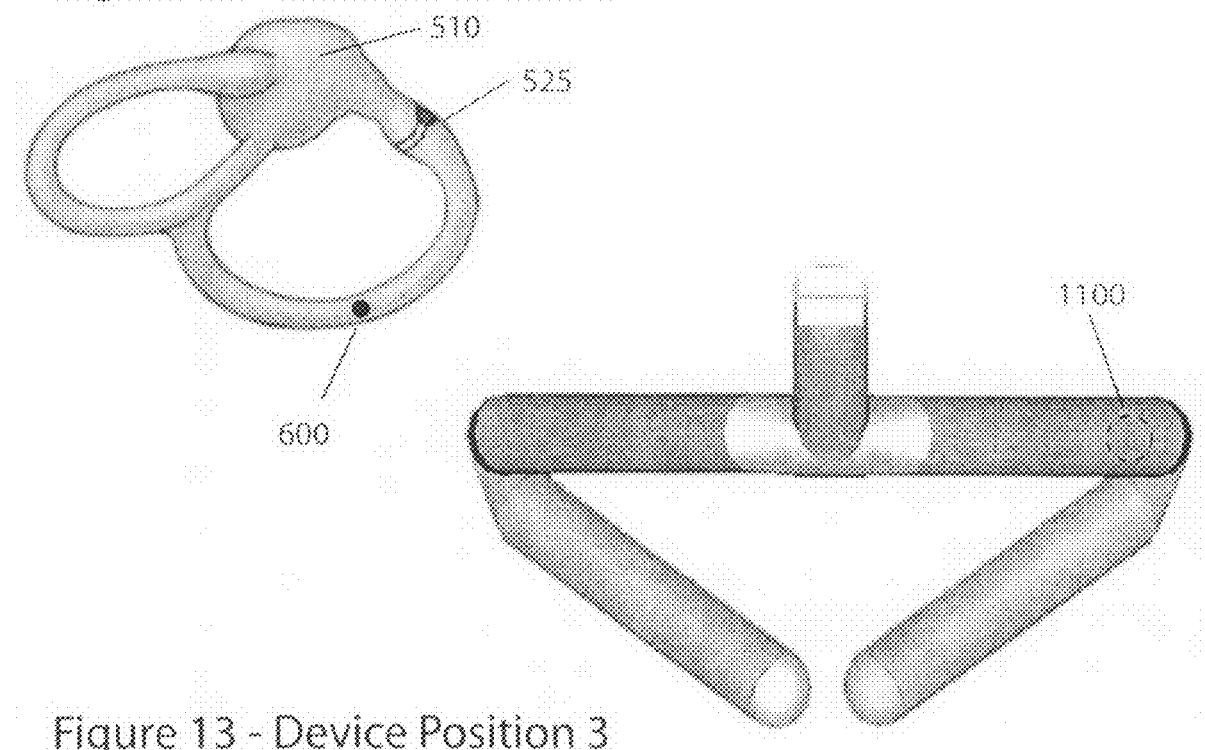
Figure 12 - Device Position 2
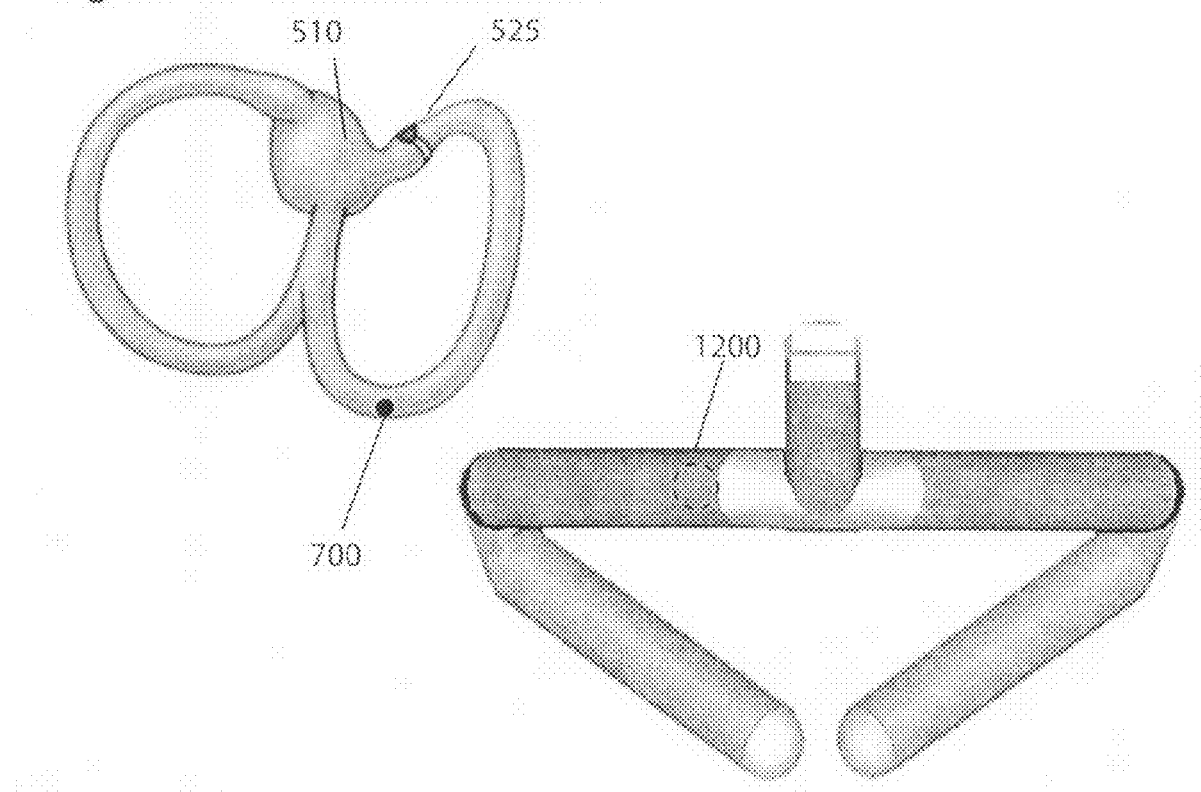
Figure 13 - Device Position 3

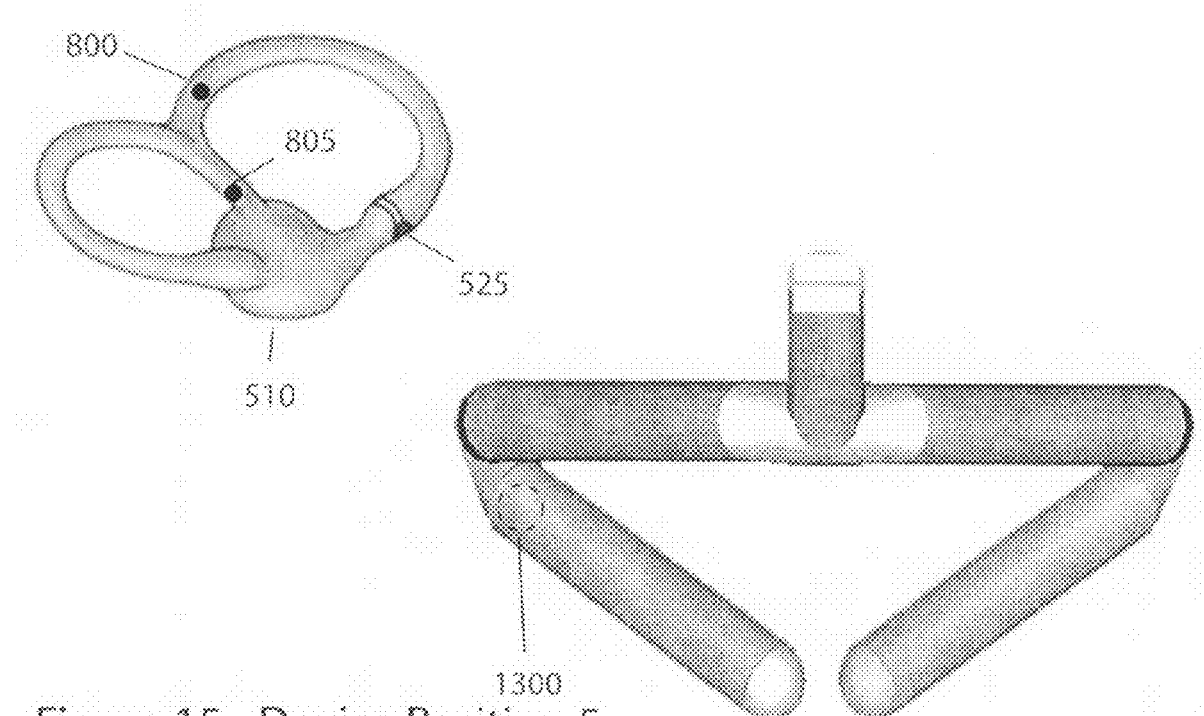
Figure 14 - Device Position 4
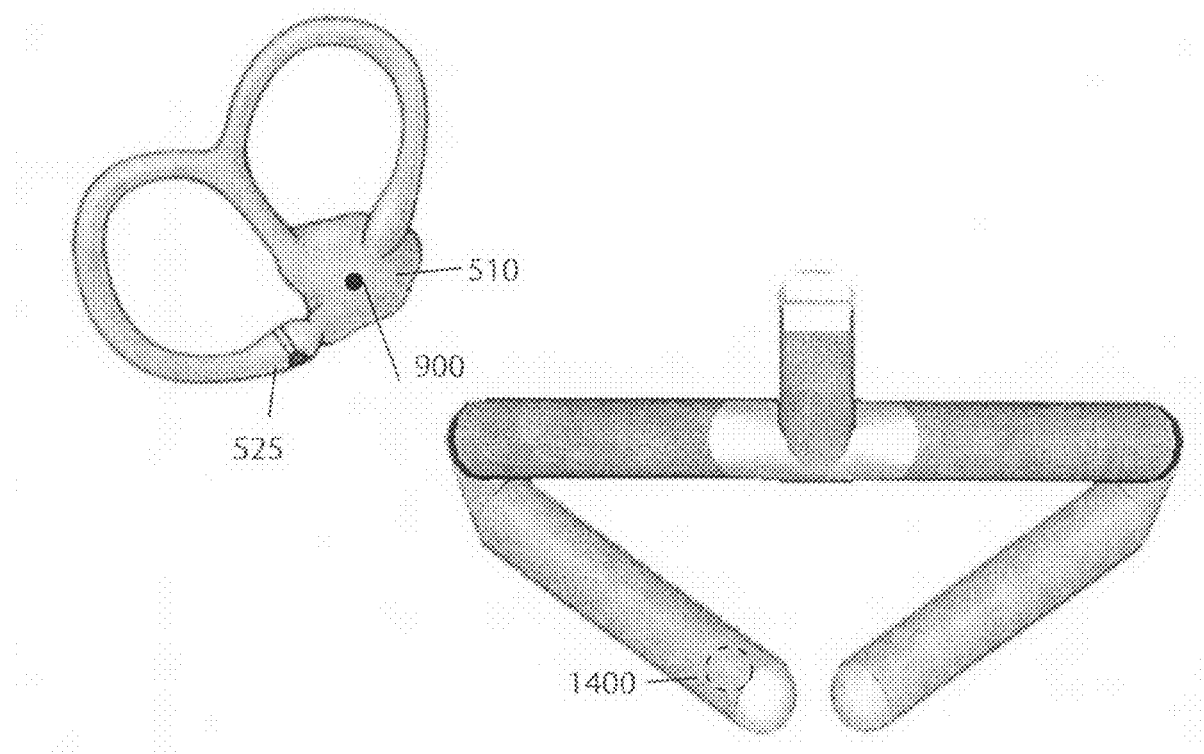
Figure 15 - Device Position 5

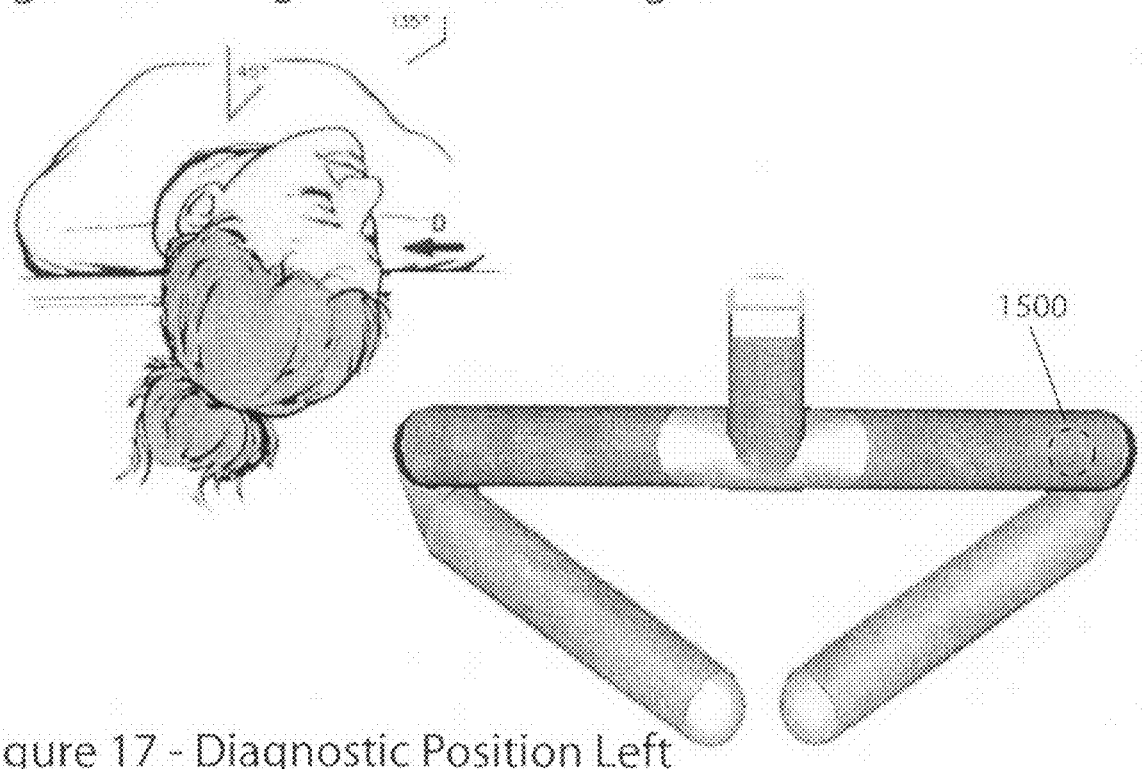
Figure 16 - Diagnostic Position Right
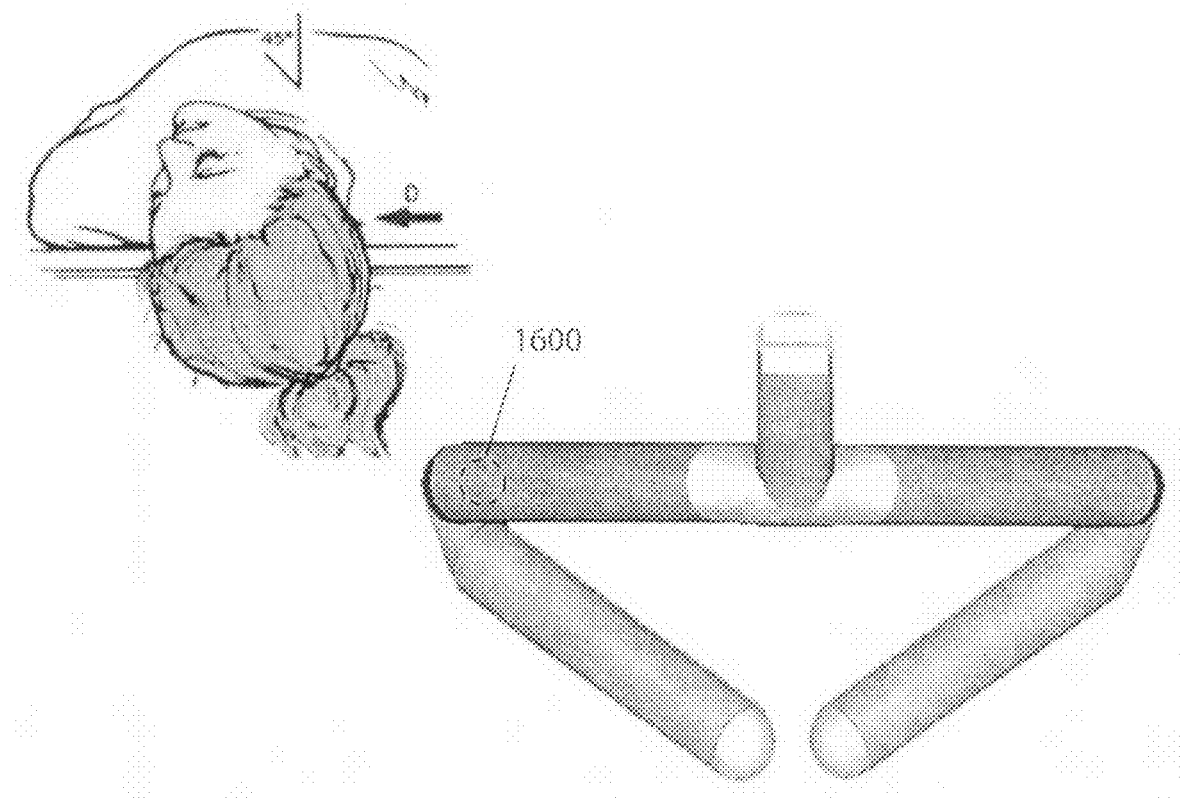
Figure 17 - Diagnostic Position Left

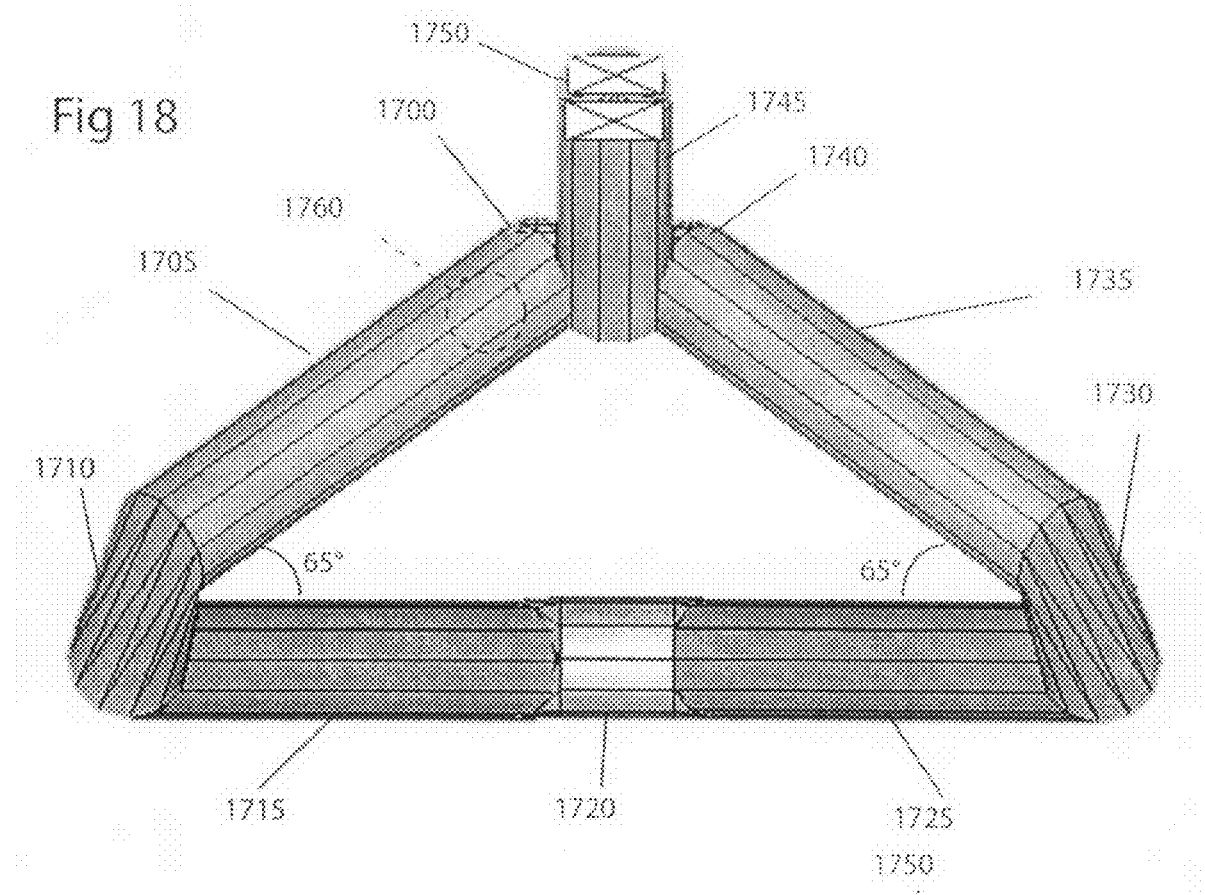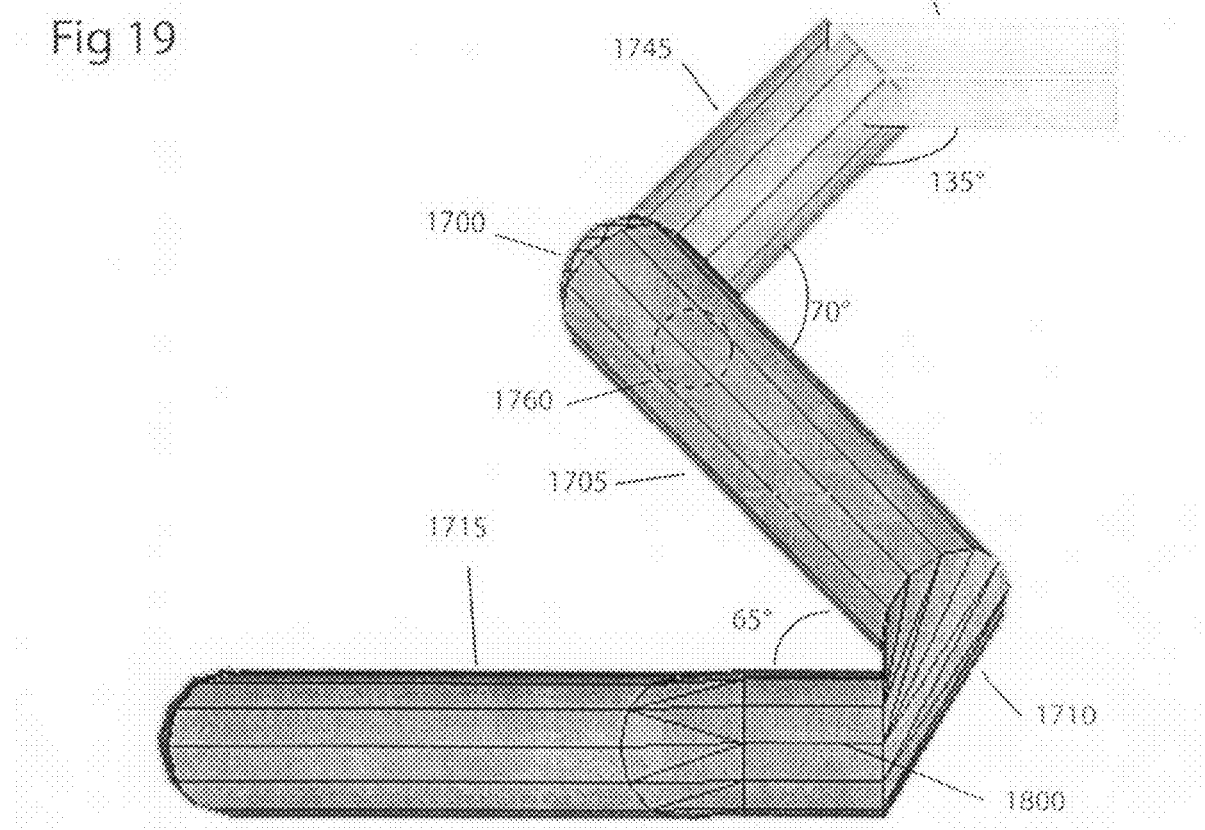

DEVICE FOR THE TREATMENT OF VERTIGO

CROSS-REFERENCES TO RELATED APPLICATIONS

This application is a non-provisional utility application which claims priority from Canadian Patent Application No. 2,546,829 filed May 12, 2006, entitled "Device for the Treatment of Vertigo" which is hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

1. Field of the Invention

The present invention relates to a medical device. More specifically, it relates to devices for the treatment of dizziness.

2. Background of the Invention

Benign paroxysmal positional vertigo (BPPV) is the most frequent cause of peripheral vertigo. (Nedzelski J M, Barber H O, McIlmoyl L. Diagnoses in a dizziness unit. *J Otolaryngol* 1986 April;15(2):101-4). It is a disease of the balance organ in the inner ear which results in short lived but frequent episodes of spinning dizziness called vertigo. Though it typically resolves over several months without any treatment, a physician guided particle repositioning maneuver can expedite the process. The two fundamental maneuver variations are based on the techniques of Semont and Epley[2, 3] who initially described the treatment of BPPV. Unfortunately, following either treatment maneuver, the condition is highly recurrent.

The current understanding of posterior canal benign paroxysmal positional vertigo (PBPPV) is that it occurs when otoconia, which are normal calcium crystals in the ear, become dislodged from the macula of the utricle, which is a part of the balance organ, and find their way into the ampullated end of the posterior semi-circular canal, which is a highly sensitive area for dizziness. Short lived rotational eye movements causing disorientation and associated vertigo results from the gravity induced movement of these calcium particles as they bump into the sensitive walls of the semicircular canals. While the duration of the disease itself is limited, the associated morbidity is high due to falls, depression, anxiety, injury and occupational hazard. Other forms of BPPV can occur when otoconia find their way into the superior and lateral canals which provide balance in the vertical and horizontal planes. These forms of BPPV are far less common and have a less symptomatic course.

The incidence of BPPV increases with age and has been estimated at greater than 10%-20% beyond the 6th decade of life. Reported recurrence rates vary widely and are dependant upon the duration of follow up. However, recurrence has been reported in as many as 30-50% of patients who undergo treatment by repositioning.

In the 1980s a series of exercises were developed which lead to a more rapid resolution of symptoms, these exercises were not therapeutic but rather caused the patient to become accustomed to the symptoms. However, these exercises required the regular induction of vertigo. After the description of new repositioning maneuvers by Semont in 1988 and Epley in 1992, effective treatments for the majority of patients became available. (Semont A, Freyss G, Vitte E. Curing the BPPV with a liberatory maneuver. *Adv Otorhinolaryngol* 1988;42:290-3) (Epley J M. The canalith repositioning procedure: for treatment of benign paroxysmal positional vertigo. *Otolaryngol Head Neck Surg* 1992 September;107(3):399-404). Beyond particle repositioning maneuvers, there is no presently known effective non-surgical treatment for BPPV. Both singular neurectomy and posterior semicircular canal occlusion are highly effective surgical procedures, but require a general anesthetic and the associated surgical morbidity.

There is a need for patients, community physicians and allied healthcare workers to be able to reproducibly perform particle repositioning maneuvers. Generally such maneuvers, while easy to perform, are somewhat difficult for patients to remember correctly. Incorrectly performed particle repositioning maneuvers are unlikely to be therapeutic.

There have been devices designed to assist in the performance of particle repositioning maneuvers. However, several difficulties exist with the design and use of these devices. These problems demonstrate the need for other devices to treat dizziness, and in particular an easy to use device which does not necessarily require a skilled individual for its operation.

There is a device for sale by Medical Surgical Innovations 1 Ocean Drive, Jupiter, Fla. which consists of a headband and skull vibrator. An adjustable neoprene headband is worn around the forehead. Attached to the headband at each temple in a plane parallel to the posterior semicircular canal is a circular channel filled with sand. The channel is designed to give feedback about the status of the patient's semicircular canals to a physician who is guiding a patient through the particle repositioning maneuver for PBPPV. As the physician guides the patient the physician can watch the particles in the channel move. This device is intended to be used by medical personnel and does not provide feedback directly to the patient. An associated vibrator is intended to be held against the skull to encourage the loose particles to move through the semicircular canal. The vibrator is a battery operated unit which is designed to be pressed against the skull and transmit kinetic vibratory energy into the skull.

U.S. Pat. Nos. 6,568,396 and 6,758,218 issued to P. Anthony describe devices using goggles. Generally speaking they consist of a set of large head worn goggles in which there is a fluid suspended, buoyancy neutral, inner spherical member upon which there is printed a sequence of numbers connected by a path. The inner member responds to gravity and magnetism and is contained within a watertight container with a sighting target printed upon it. The housing is held at a fixed distance close to the eye by a set of goggles which also contain a lens which is necessary to allow the patients wearing the device to focus upon the inner member. The user moves their head such that the outer housing moves with respect to the inner member. By aligning the sighting mark with the numbers printed on the inner member of the device the patient can follow the path traced out and complete a particle repositioning maneuver. Several inner members exist to diagnosis and treat various types of BPPV. A new inner member is required for each task related to BPPV and its diagnosis. The large, bulky and expensive outer housing is required to contain the inner member and the lenses required for viewing. These devices are complex and relatively difficult to use as there are a number of parts to exchange and align. In addition, these devices are not useful for providing feedback to medical or assisting personnel.

U.S. Pat. No. 6,029,670 describes a helmet with flat sides to assist in positioning a patient correctly. This device is only useful for one skilled in the particle repositioning maneuver. The device's intention is to ensure consistency between patient maneuvers. It is not a diagnostic device, nor does it provide visual feedback to either the user or physician.

A device described by Epley and Lempert consisting of a mechanical rotating chair has been used in some institutional settings. The rotational chair is akin to an amusement park ride wherein the rider is spun in 3 axes. The chair is connected to a computer into which can be input the exact nature of the semicircular canals. With this information the computer can calculate a path which will guide any loose otoconia out of the offending areas. By hydraulic and mechanical means controlled by the computer the chair is moved through this pre-calculated pathway. There exist only a very few of these devices worldwide as they are very large and expensive. They are typically used in tertiary care hospitals with a special interest in vestibular disorders.

BRIEF SUMMARY OF THE INVENTION

It is an object of the present invention to provide a device for the diagnosis and treatment of dizziness, comprising: a tube having a first end and a second end and containing fluid; a communicating means in the tube for passage through the tube and communicating information regarding a user's head position; means for attaching the tube to the user's head whereby the user can directly observe the communicating means in the tube; wherein the shape of the tube only permits passage of the communicating means from the first end to the second end of the tube or vice versa when the tube is attached to the user's head if the user performs a particle repositioning maneuver.

As such the present invention provides an easy to use device for the diagnosis and treatment of BPPV, which can provide feedback regarding a particle repositioning maneuver to both a user and medical or assisting personnel.

In addition, another object of the present invention is to provide a form of physiotherapy where patients have suffered injury to the semicircular canals from trauma or infection and subsequent disequilibrium or dizziness. During the course of the PRM all three semicircular canals are stimulated. In cases where patients have suffered injury to the semicircular canals from trauma or infection the invention can be used as a form of physiotherapy which is repeatable and quantifiable.

In different embodiments of the present invention the communicating means can be a bead, a bubble of air or other gas or a second immiscible fluid.

It is another object of the present invention to provide a kit comprising a device for the treatment of dizziness and instructions for completing a particle repositioning maneuver.

BRIEF DESCRIPTION OF THE SEVERAL VIEWS OF THE DRAWINGS

FIG. 2 depicts a front elevation of an embodiment of the present invention.

FIG. 3 depicts a side elevation of an embodiment of the present invention.

FIG. 6 depicts the upright position number 1 of a particle repositioning maneuver (PRM). Included is a diagram of the head as well as the posterior semicircular canal and the relative position of the loose otoconia in the canal.

FIG. 7 depicts the supine position number 2 of a right sided PRM. Included is a diagram of the head and the posterior semicircular canal and the relative position of the loose otoconia in the canal.

FIG. 8 depicts the supine position number 3 for a right sided PRM. Included is a diagram of the head and the posterior semicircular canal and the relative position of the loose otoconia in the canal.

FIG. 9 depicts the supine position number 4 of a PRM for the right side. Included is a diagram of the head and the posterior semicircular canal and the relative position of the loose otoconia in the canal.

FIG. 10 depicts the end upright position number 5 of a PRM for the right side. Included is a diagram of the head and the posterior semicircular canal and the relative position of the loose otoconia in the canal.

FIG. 11 depicts the position of a particle in an embodiment of the present invention and a diagram of the position of the otoconia in the posterior semicircular canal during position 1 of a PRM for a right sided maneuver.

FIG. 12 depicts the position of a particle in an embodiment of the present invention and a diagram of the position of the otoconia in the posterior semicircular canal during position 2 of a PRM for a right sided maneuver.

FIG. 13 depicts the position of a particle in an embodiment of the present invention and a diagram of the position of the otoconia in the posterior semicircular canal during position 3 of a PRM for a right sided maneuver.

FIG. 14 depicts the position of a particle in an embodiment of the present invention and a diagram of the position of the otoconia in the posterior semicircular canal during position 4 of a PRM for a right sided maneuver.

FIG. 15 depicts the position of a particle in an embodiment of the present invention and a diagram of the position of the otoconia in the posterior semicircular canal during position 5 of a PRM for a right sided maneuver.

FIG. 16 depicts a diagnostic position for BPPV on the right side.

FIG. 17 depicts a diagnostic position for BPPV on the left side.

FIG. 18 is a front elevation of an embodiment of the present invention using a bubble of air instead of a particle.

FIG. 19 is a side elevation of an embodiment of the present invention using a bubble of air.

DETAILED DESCRIPTION OF THE INVENTION

In one embodiment, the present invention is a device which can attach to any common hat worn by a patient. The device then provides visual feed back to both the patient and any observer/assistant about head position and the status of the particles within the patient's posterior semicircular canal.

The device attaches to the user's head in order to provide a visual analogue for the relative position of the user's own otoconia. As such it enables either the user or an observer to easily guide the particle through the tube and thus treat BPPV.

In this embodiment the present invention comprises a tube, typically of clear plastic, filled with a fluid with a certain degree of viscosity which may be clear and non-toxic. In various embodiments this tube can be bent into a number of specific and unique shapes which loosely represent either one or both posterior semicircular canals. There is a communicating means, usually a plastic particle, particles, bead, immiscible fluid droplet or air bubble within the tube which has characteristics related to its buoyancy and resistance within the fluid that approximate the characteristics of otoconia in the semicircular canal. Means for attaching the tube to a user's head includes a clip that attaches to the brim of a hat. The hat is retained on the head by any common means known in the art, including by an elastic strap. The clip or other attaching means is a particular length and angle which positions the tube such that the communicating means can be seen, in focus, by a patient through the tube and such that the tube is correctly oriented with the patient's own semicircular canals. The device is preferably maintained at a fixed distance from the patient's eyes.

It is understood that the specific measurements and angles disclosed in the following description may be varied. The length of tubing is dependent on the viscosity of the fluid within the tubing; the more viscous the fluid, the shorter the lengths of tubing, and the less viscous the fluid, the longer the lengths of tubing. Preferably the tubing is suitably sized so that it can be comfortably worn by a patient and so that the patient can easily see the entire device.

Similarly, the angles specified are approximate. Some variability, for example, 10 or 20 degrees above or below the specified angles may be feasible.

The shape of the device may also be adapted to suit the particular maneuver to be performed. In the examples provided herein, the maneuver is a particle repositioning maneuver. Other possibilities might be a Liberatory or Semont maneuver, or Brandt Daroff exercises.

Figure 1:
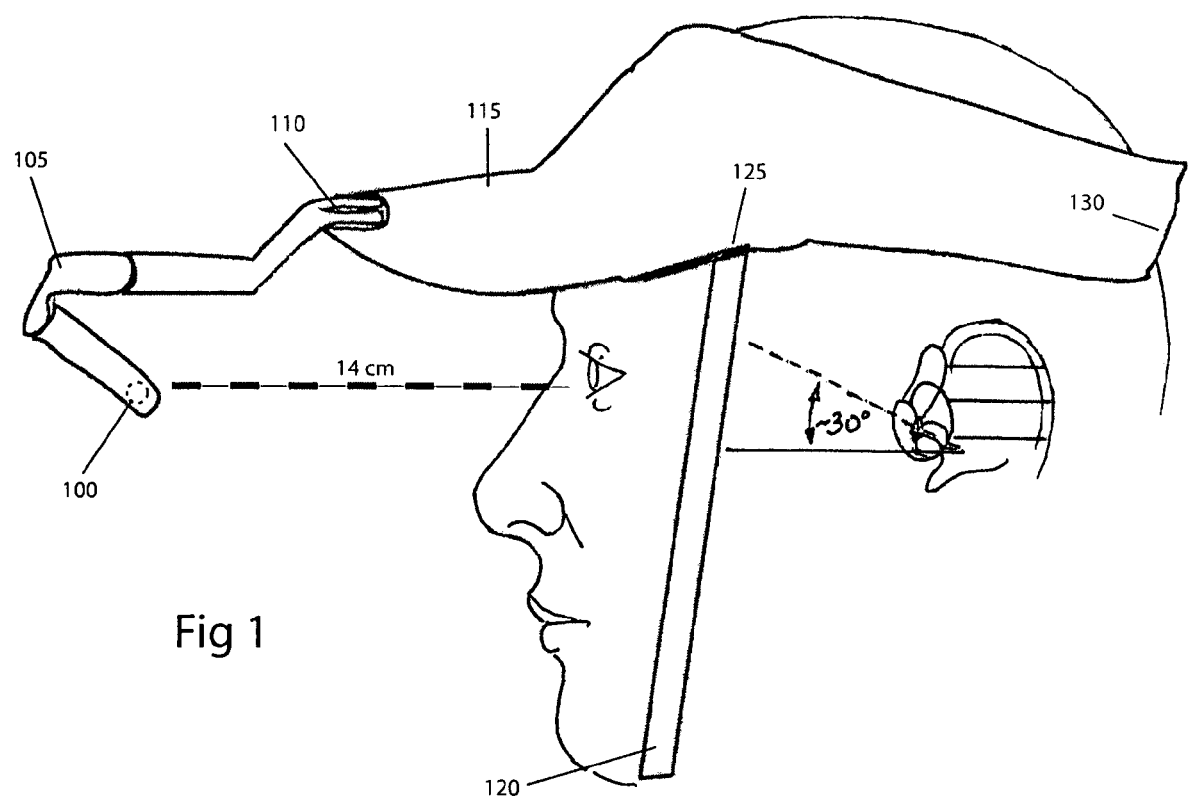
FIG. 1 depicts an overview of an embodiment of the present invention.

FIG. 1 depicts an overview of the components of this embodiment. This includes a tube 105, particle 100, clip 110, elastic strap 120, elastic strap attachment 125 and adjustable hat 130 with brim 115. The tip of the lower aspect of the tube 105 is approximately 14 cm from the user's eye. The minimum distance of visual field fusion in most humans is approximately 12 cm. Objects closer than this are generally difficult to visualize with both eyes. Clip 110 provides the necessary distance from the face as well as aligning the particle 100 substantially with the eye. The tube 105 comprises a clear plastic pipe, typically acrylic, which is approximately 5/16" in external diameter and 3/16" in internal diameter which is filled with a fluid such as a clear non-toxic petroleum distillate. Sections of the tube may be color coded. The shape of the tube is further described below. The particle can be a brightly colored 3 mm poly vinyl bead with a 1 mm hole drilled through the center. The density of this bead is slightly greater than water. The nature of the interaction between the particle, tube and fluid simulate the fluid and particle dynamics encountered in the semicircular canal.

Due to the shape and properties of the tube and fluid the bead moves only in positions that stimulate the posterior canal. The bead moves at a similar speed and for a comparable duration to the patients own otoconia. In this fashion, patients directly observe or watch the bead in front of them and guide it through the entire length of the tube. As such, it communicates information regarding the user's head position to the user. In addition, other individuals present, including those who may be guiding the user through a particle repositioning maneuver (PRM) may also directly observe the bead. The action of moving the bead from one end to the other necessitates that the patient performs and moves through the PRM. The design of the device is also simple and allows it to perform its function regardless of the side of the disease.

FIG. 2 depicts this embodiment in a front elevation. The shape of tube 105 facilitates the performance of a particle repositioning maneuver and treatment of posterior BPPV (PBPPV). The required length of tube arms may vary depending upon the viscosity, density and diameter of the fluid, particle and tube respectively. Latency of onset is a well recognized characteristic of BPPV and may last more than 5-10 seconds. It is important that progress of bead in the device reflects the current state of the patient's otoconia and does not move forward without patient input. The bends within the tube mimic characteristics of the semicircular canals but also prevent the particle from moving on to the next section of the tube without the patient conducting the next part of the PRM.

Sphere 200 is a colored tip which indicates the left start point for the particle 100. Beginning section 205 is 5.5 cm long and angulated down from first transition section 215, in a vertical plane by 65 degrees. All angles and lengths are approximate and as noted may vary depending on the viscosity, density, and diameter of the fluid, particle and tube respectively. The length and angle should create a situation such that it takes greater than 10 seconds for particle 100 to move from position 200 to first elbow section 210 during a PRM. First elbow section 210 is the "red zone" for a left sided diagnostic maneuver. When the particle is in this section of the tube patients with BPPV will likely experience vertigo. First elbow section 210 can be color coded red and is 2 cm in length. First transition section 215 is 5.5 cm in length and oriented in a horizontal plane. The length ensures proper progress through the PRM. Clip section 225 is 7 cm in length and is attached to the clip. Clip section 225 is angulated 45 degrees above the horizontal and ends in the clip which facilitates attachment to a hat by means of a pressure friction fit. 225 is approximately 7 cm long to provide the required distance from the eye to allow proper focus. The 45 degree angle allows the device to be in the center of the user's field of view. Second transition section 230 is 5.5 cm long and represents the mirror image of first transition section 215. Similarly second elbow section 235 mirrors first elbow section 210 and represents the "red zone" for a right sided maneuver and is color coded red. Second elbow section 235 is again 2.5 cm in length. Terminating section 240 is 5.5 cm in length and a mirror image of beginning section 205. Sphere 245 represents the final end point of particle 100 after a completed maneuver and can be color coded as the start point for a right sided maneuver.

FIG. 3 depicts a side elevation of this embodiment. As can be seen in this figure beginning section 205 is 65 degrees below the horizontal line drawn by first transition section 215. First intermediate section 300 is 2 cm in length. Clip section 225 is oriented 45 degrees above the horizontal. First elbow and first intermediate sections consist of two distinct sections, or may alternatively be combined into a single section, which may be called the first middle section.

Figure 4:
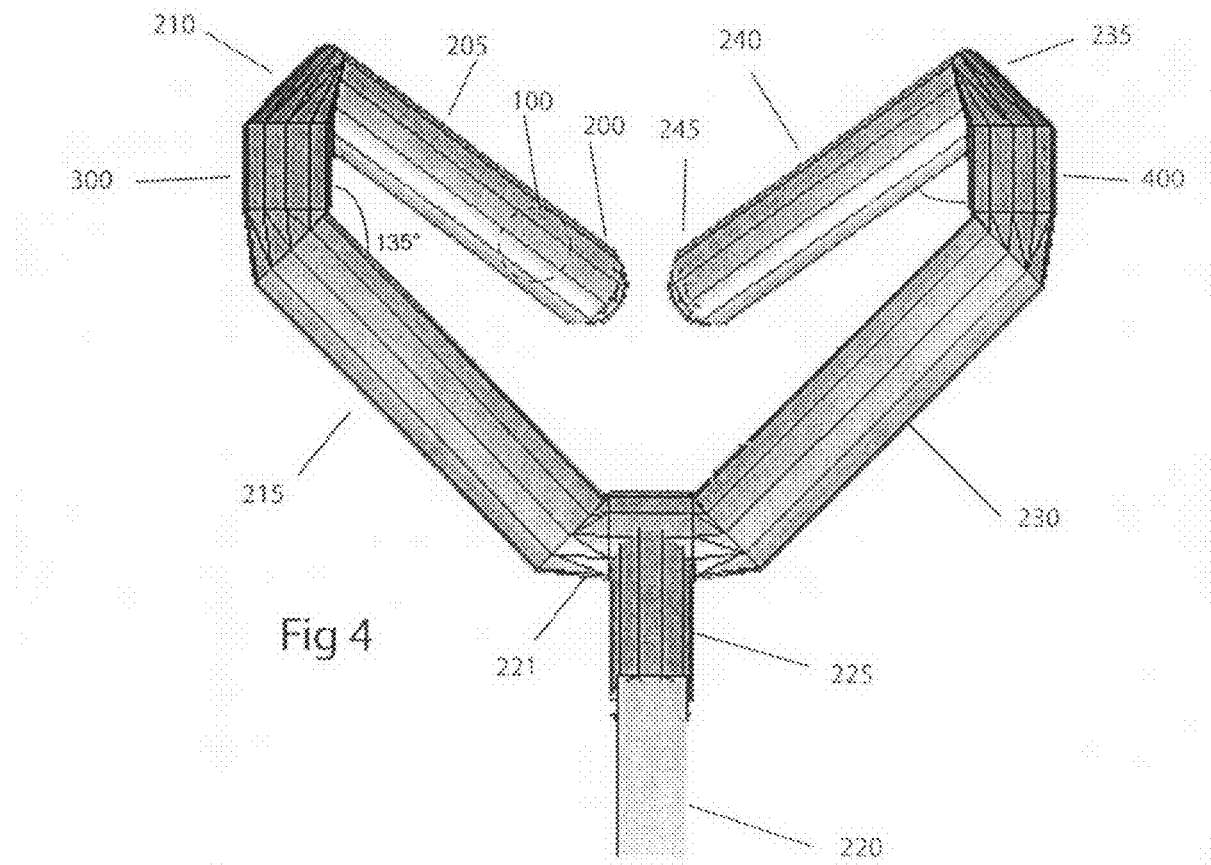
FIG. 4 depicts a plan view of an embodiment of the present invention.

FIG. 4 depicts a plan view of this embodiment. First and second transition sections 215 and 230 are oriented 90 degrees from each other. First transition section 215 is 135 degrees from the vertical in relation to first intermediate section 300.

Figure 5:
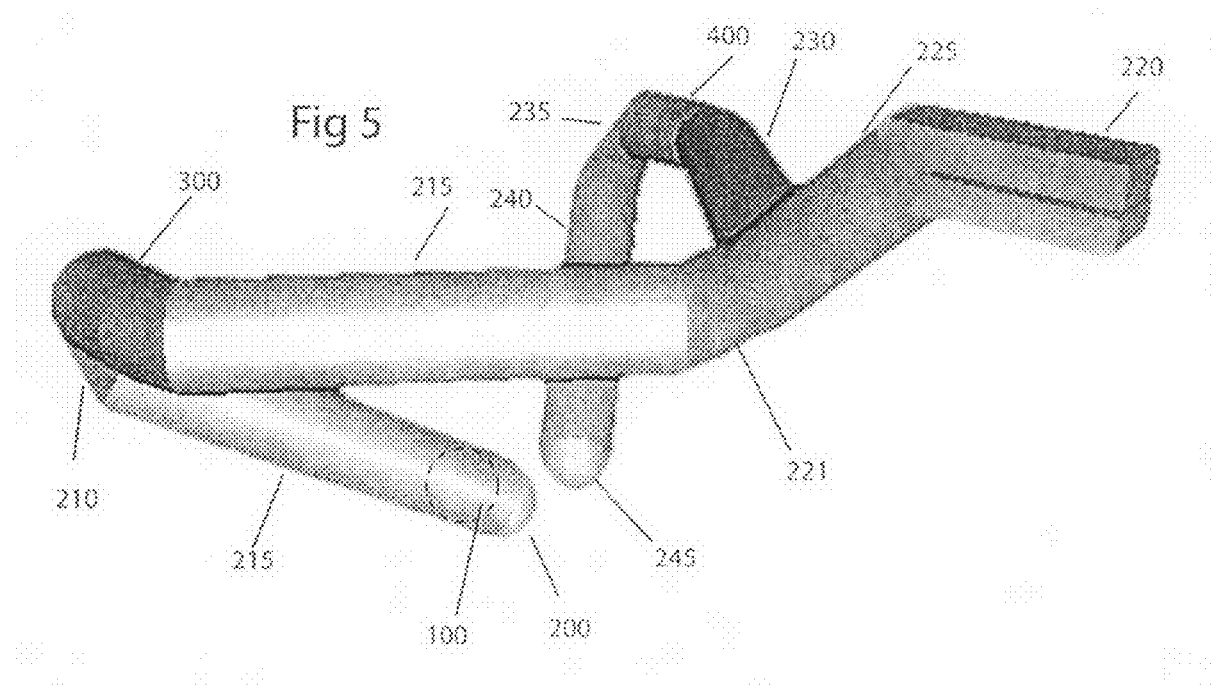
FIG. 5 depicts a perspective view of an embodiment of the present invention.

FIG. 5 depicts a perspective view of this embodiment.

A PBPPV Particle Repositioning Maneuver

FIG. 6 depicts a user in the upright position number 1 of a particle repositioning maneuver (PRM). The maneuver consists of 5 positions. Upright, supine with the head turned to one side, supine with the head turned to the other side, rolled onto the second shoulder and finally upright again. The orientation of the user's posterior and superior semicircular canals is also depicted. 520 represents the common crus of these two canals. 515 is the superior semicircular canal. The particle 500 is in the posterior semicircular canal. 510 is the utricle of the semicircular canal which is the end target for the particle. 505 is the ampulla which prevents the particle from entering the utricle from the ampullated 525 end.

FIG. 7 depicts a user in position 2 of the PRM for right sided therapy, which is also a diagnostic position. The user's head is extended to 135 degrees from the vertical and turned 45 degrees to the right. The particle 600 has moved along the posterior semicircular canal away from the ampulla 525 toward the utricle 510.

FIG. 8 depicts the user in position 3 of the PRM with their head turned 45 degrees to the left. 700 shows the relative location of the particle within the posterior semicircular canal. Again the particle has moved away from the ampullated end of the canal 525 toward the utricle 510.

FIG. 9 depicts the user in position 4 of the PRM where they have rolled onto their left shoulder and are looking at the ground. 800 shows the relative location of the particle as it is emptied into the common crus 805 just before the utricle 510.

FIG. 10 depicts position 5 of the PRM with the patient again in an upright position. The particle 900 is now in the utricle 510.

Use of the Described Embodiment for a Particle Repositioning Maneuver Treatment of BPPV The design of the tube allows for the PRM to be conducted in either direction which allows for the maneuver to be conducted for each ear without adjusting or changing the device. This design ensures that it is impossible to succeed in moving the particle though the tube without performing the required steps.

Unlike other devices this invention is suitable to be used by both the patient and any observer or assistant. By positioning the device far enough in front of the patient that they can sharply focus upon the particle it obviates the need for a sighting lens. In this fashion no other head gear is required and an observer may also watch the particle during the maneuver. This is especially important to the elderly who may require physical assistance to complete the maneuver. Also this allows for those physicians not skilled in this maneuver to participate in the care of their patients and guide them through the PRM in a correct and therapeutic fashion. In this way the device provides relevant and real time feedback to both patient and physician/assistants.

The user is instructed to position the particle in the end of the tube which corresponds to the side on which they have diagnosed BPPV. In other words, if they have right sided vertigo then the particle begins in the right side of the tube and vice versa.

The user is then instructed to wear the device and secure the hat with an elastic strap. They are then instructed to maneuver the particle within the tube from one end to the other by performing a PRM it should be noted that any series of head movements which will move the particle through the tube and thereby move the otoconia through the semicircular canals and into or toward the utricle is an acceptable PRM. This is most easily accomplished by the user lying down with their neck extended over a pillow and turning their head (in this case) to the right. The particle then moves along the tube into the "red zone". The user typically experiences vertigo during this phase and is instructed to remain stationary until the sensation passes. Once the resolution of vertigo is complete the user can most easily move the particle along by turning their head to the other side about 45 degrees. The particle then continues along the tube. The user must then roll onto their left shoulder and look towards the ground for the particle to continue its motion. Finally the user must sit up for the particle to come to rest at the other end of the tube.

By maneuvering the particle within the tube from one end to the other the patient maneuvers their own otoconia out of the affected end of the posterior semicircular canal and back into the utricle where no symptoms are encountered.

With greater detail, FIGS. 11-15 depict the relative correlation of the above described 5 PRM movements associated with treating BPPV, the device itself and the semicircular canals. In FIG. 11, 500 represents the particle in the ampullated end of the canal. 1000 denotes the start position of the particle in the device for a right sided maneuver. A user wearing the device as in FIG. 11 is currently upright in position 1 as described in FIG. 6. The user is instructed to move the particle in the tube by moving their head into position 2 of the PRM for the right side.

FIG. 12 depicts the semicircular canal and device when the user is in position 2 of a right sided PRM as described in FIG. 7. The user's head is extended 135 degrees and turned 45 degrees to the right. 1100 denotes the location of the particle in the device during this position. 600 represents the location of the particle in the semicircular canal during this position. The user with PBPPV will likely experience vertigo in this position which is also useful for diagnosis. The user is instructed to remain in this location until the particle in the tube has stopped moving or the vertigo subsides, which ever happens last.

FIG. 13 depicts the semicircular canal and device when the user is position 3 of a right sided PRM as described in FIG. 8. The user's head is still extended but their head is now turned 45 degrees to the left. 1200 denotes the location of the particle in the device during this position. 700 represents the location of the particle in the semicircular canal during this position. Again the user is instructed to remain in this position until the particle in the tube stops moving.

FIG. 14 depicts the semicircular canal and device when the user is position 4 of a right sided PRM as described in FIG. 9. The user is rolled up onto their left shoulder and is looking at the ground. 1300 denotes the location of the particle in the device during this position. 800 represents the location of the particle in the semicircular canal early during this position. 805 represents the later location of the particle during this position. The user is again instructed to remain in this position until the particle in the tube has ceased to move.

FIG. 15 depicts the semicircular canal and device when the user is position 5 of a right sided PRM as described in FIG. 10. The user is again sitting up. 1400 denotes the location of the particle in the device during this position. 900 represents the location of the particle in the semicircular canal during this position.

A BPPV Diagnostic Method

This embodiment of the invention is useful for the diagnosis of BPPV. The tube has two "red zones" in which vertigo is likely to be encountered. The user is instructed to wear the device and focus on the particle within the tube. The user is instructed to move the particle within the tube into the "red zone" by lying on their back and turning their head to one side. In a diagnostic position the patient watches the particle within the tube. If, once the particle enters the red zone, the patient experiences vertigo then BPPV can be diagnosed on that side. If, however, no vertigo is experience then BPPV is not the likely etiology on that side. The maneuver can then be repeated on the other side. In either case, a patient experiencing vertigo should observe the particle. When the particle ceases to move the vertigo should stop. If the vertigo continues much past the cessation of movement then another etiology of vertigo should also be sought.

FIG. 16 depicts the diagnostic position for a right sided disease state. The patient position and the location of the particle 1500 in the device are shown. The user is instructed to wear the device with the particle in the right end of the tube 245. The user is asked to lie down with their neck extended and turned to the right side. By the time the particle in the tube reaches section 235 and the "red zone" any user with active BPPV in the right side will experience vertigo. Vertigo associated with BPPV should not occur unless the particle is in the "red zone".

FIG. 17 depicts the diagnostic position for a left sided disease state. The patient position and the location of the particle 1600 in the device are shown. The user is instructed to wear the device with the particle in the left end of the tube 200. The user is asked to lie down with their neck extended and turned to the left side. By the time the particle in the tube reaches section 210 and the "red zone" any user with active BPPV in the left side will experience vertigo. Vertigo associated with BPPV should not occur unless the particle is in the "red zone".

Vestibular Rehabilitation

Vestibular rehabilitation is exercise for the balance organ which is useful following injury, and consists of repeated head motions designed to induce a fluid wave within the semicircular canal and produce stimulation which is useful to the brain and improves its ability to accommodate the damaged vestibular apparatus. The device similarly is designed to stimulate the posterior semicircular canal and also the other canals. Repeated use of this device as described above guides the user in stimulating multiple semicircular canals. It provides feedback and a method for monitoring and quantifying progress and recovery.

The user is instructed to wear the device on their hat and maneuver the particle within the tube from one side to the other. In this case it does not matter on which side the particle starts. The user is instructed to repeat this maneuver as many times as possible. Typically patients with vestibular injury are unable to complete these sorts of tasks due to nausea and an unsettling sensation of motion called disequilibrium. Repeating the maneuver stimulates recovery of the brain's ability to process information from damaged semicircular canals. Counting the number of times the maneuver is completed during treatment quantifies the rate of recovery.

Other Embodiments

FIG. 18 depicts another embodiment of the present invention in which a bubble of air or other gas is used as a communicating means instead of a particle. Other embodiments may include an apparatus to illuminate the tube and a particle within. The particle may also be brightly colored or contain pigment sensitive to UV light to enhance its visibility. The particle may instead be a second immiscible fluid with chemical properties such that it acts like a bead within the tube. This immiscible fluid may also be brightly colored to aid in visibility.

FIG. 18 depicts an embodiment using a bubble 1760 in a front elevation. The device comprises a tube with fluid and a bubble 1760 inside. Sphere 1700 may be a colored tip of the tube which indicates the right start point for the bubble 1760. Beginning section 1705 is 5.5 cm long and angulated up from first transition section 1715, in a vertical plane by 65 degrees. Angles and lengths are again approximate. The length and angle create a situation such that under the right circumstances it takes greater than 10 seconds for bubble 1760 to move from position 1700 to section 1715. First elbow section 1710 could be colored red to indicate a "red zone" for a right sided diagnostic maneuver. This section is 2 cm in length. First transition section 1715 is 5.5 cm in length and oriented in a horizontal plane. The length ensures proper progress through a PRM. Clip section 1745 is 7 cm in length and is attached to the clip. It is angulated 45 degrees above the horizontal and ends in clip 1750 which facilitates attachment to a hat brim by means of a pressure friction fit. Clip section 1745 is approximately 7 cm to provide the required distance from the eye to allow proper focus. The 45 degree angle allows the device to be in the center of the user's field of view. Second transition section 1725 is 5.5 cm long and represents the mirror image of first transition section 1715. Similarly second elbow section 1730 mirrors first elbow section 1710 and represents the "red zone" for a left sided maneuver and is color coded red. Second elbow section 1730 is again 2.5 cm in length. Terminating section 1735 is 5.5 cm in length and mirrors beginning section 1705. Sphere 1740 represents the final end point of bubble 1760 after a completed maneuver and is color coded as the start point for a left sided maneuver.

FIG. 19 depicts the side elevation of this embodiment. Beginning section 1705 is 65 degrees above the horizontal line drawn by first transition section 1715. First intermediate section 1800 is 2 cm in length. Clip section 1745 is oriented 45 degrees above the horizontal. The clip 1750 is horizontal. First elbow and first intermediate sections may be separate, or may be combined into a single section, the first middle section.

Figure 20:
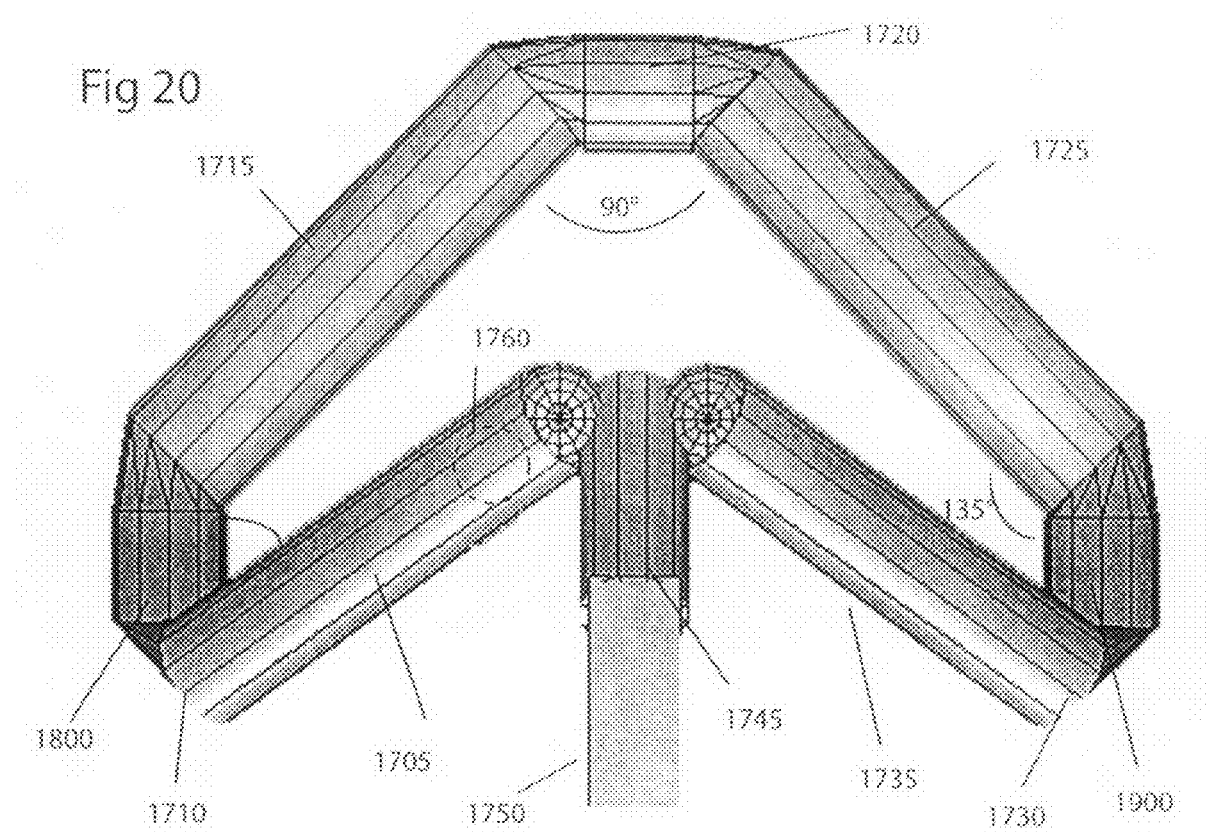
FIG. 20 is a plan view of an embodiment of the present invention using a bubble of air.

FIG. 20 depicts a plan view of this embodiment. First and second transition sections 1715 and 1725 are oriented 90 degrees from each other. First transition section 1715 is 135 degrees from the vertical at first intermediate section 1800. Terminating section 1735 is continuous with the second intermediate section 900 which is the mirror image of first intermediate section 1800.

Figure 21:
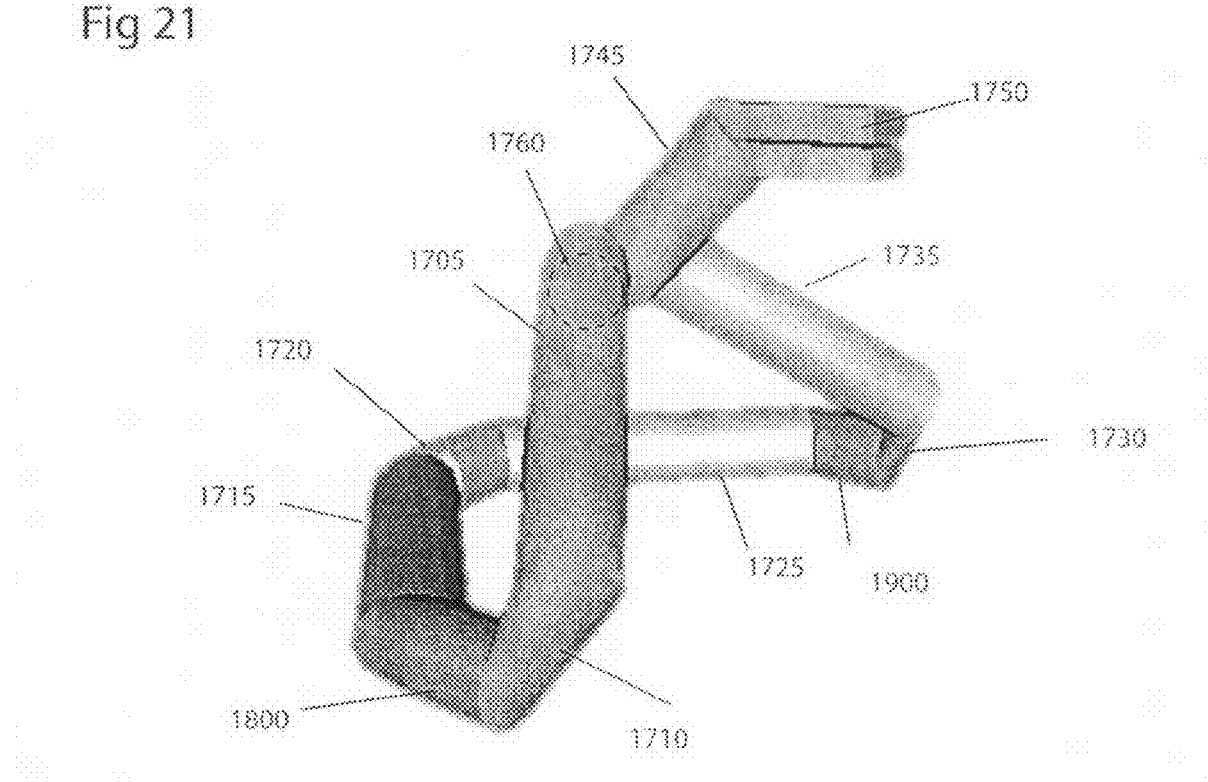
FIG. 21 is a perspective view of an embodiment of the present invention using a bubble of air.

FIG. 21 depicts a perspective view of this embodiment.

Method of Use of An Embodiment with a Bubble

The method of use of this embodiment is similar to the previous description, however, instead of a particle or bead a bubble of gas is used. This requires that the tube be oriented upside-down and backwards compared to the previous description. It further requires that a left sided maneuver be started with the bubble in the right side and vice versa. 1760 denotes the start position of the bubble in the device for a right sided maneuver. The user wearing the device begins in the upright in position 1 as described in FIG. 6. The user is instructed to move the bubble in the tube by moving their head into position 2 of the above described PRM for the right side.

In position 2 of the PRM the bubble would have moved to first elbow section 1710 as seen in FIG. 18. The user's head is extended 135 degrees and turned 45 degrees to the right. The user will likely experience vertigo in this position. The user is instructed to remain in this location until the bubble in the tube has stopped moving or the vertigo subsides, which ever happens last.

In position 3 of a right sided PRM as described in FIG. 8 the bubble with move into section second transition section 1725. The user's head is still extended but their head is now turned 45 degrees to the left. Again the user is instructed to remain in this position until the bubble in the tube stops moving.

In position 4 of a right sided PRM as described in FIG. 9 the bubble moves in to second elbow section 1730. The user is rolled up onto their left shoulder and is looking at the ground. The user is again instructed to remain in this position until the particle in the tube has ceased to move.

Finally in position 5 of a right sided PRM as described in FIG. 10 the bubble moves to sphere 1740. The user is again sitting up. The motion of the user is identical to the previous embodiment but the motion of the bubble is opposite to the previous embodiment.

BPPV Diagnostic Method for this Embodiment

The diagnosis of disease in this embodiment is similar to the previous embodiment. For the right ear, as seen in FIG. 16, the patient lies with their head turned 45 degrees to the right and in 135 degrees of neck extension. The bubble 1760 moves from sphere 1700 to first elbow section 1710. The user is instructed to wear the device with the bubble in the left end of the tube to diagnose right sided disease. By the time the bubble in the tube reaches first elbow section 1710 and the "red zone" any user with active BPPV in the right side will experience vertigo. Vertigo associated with BPPV should not occur unless the particle is in the "red zone".

For the left ear, as seen in FIG. 17, the patient lies with their head turned 45 degrees to the left and in 135 degrees of neck extension. The bubble 1760 moves from sphere 1740 to second elbow section 1730. The user is instructed to wear the device with the bubble in the right end of the tube to diagnose left sided disease. By the time the bubble in the tube reaches second elbow section 1730 and the "red zone" any user with active BPPV in the left side will experience vertigo. Vertigo associated with BPPV should not occur unless the particle is in the "red zone".

Thus, although there have been described particular embodiments of the present invention of a new and useful Device for the Treatment of Vertigo, it is not intended that such references be construed as limitations upon the scope of this invention except as set forth in the following claims.

What is claimed is:

1. A device for the treatment of dizziness, comprising:
   a tube having a first end and a second end and containing fluid;
   a communicating means in the tube for passage through the tube and communicating information regarding a user's head position;
   means for attaching the tube to the user's head whereby the user can directly observe the communicating means in the tube;
   wherein the shape of the tube only permits passage of the communicating means from the first end to the second end of the tube or vice versa when the tube is attached to the user's head if the user performs a particle repositioning maneuver.

2. A kit comprising:
   the device of claim 1 and instructions for performing a particle repositioning maneuver.

3. The device of claim 1 wherein the communicating means is a polyvinyl bead.

4. The device of claim 1 wherein the fluid is a petroleum distillate.

5. The device of claim 1 wherein the communicating means is a bubble of gas.

6. The device of claim 1 wherein the communicating means is a liquid immiscible with the fluid.

7. The device of claim 1 wherein the means for attaching the tube to the user's head comprises:
   a hat;
   a clip affixed to the tube for attachment to the brim of the hat; and
   an elastic strap attached to the hat.

8. The device of claim 1 wherein the shape of the tube resembles the shape of at least one posterior semicircular canal.

9. The device of claim 8 wherein the tube comprises beginning, first middle, and first transition sections.

10. The device of claim 8 wherein the beginning section is located at the first end of the tube, the first transition section is located at the second end of the tube, and the first middle section connects the beginning section to the first transition section.

11. The device of claim 10 wherein the first middle section comprises a first elbow section and a first intermediate section.

12. The device of claim 11 wherein the angle between the beginning section and the first transition section is approximately 65 degrees.

13. The device of claim 11 wherein the angle between the first intermediate section and the first transition section is approximately 135 degrees.

14. The device of claim 11 wherein the tube further comprises terminating, second elbow, second intermediate and second transition sections which are arranged respectively in a mirror image of the beginning, first elbow, first intermediate and first transition sections.

15. The device of claim 10 further comprising a clip section which connects the tube to the means for attaching the tube to the user's head.

16. A method of diagnosing benign paroxysmal positional vertigo in a patient comprising the steps of:
   (1) affixing the device of claim 1 to a patient;
   (2) guiding the patient towards and into a diagnostic position; and
   (3) observing the communicating means of the device to determine when the diagnostic position has been reached and maintained for a sufficient period of time.

* * * * *